United States Patent [19]

Asano et al.

[11] Patent Number: 5,485,752

[45] Date of Patent: Jan. 23, 1996

[54] APPARATUS FOR DETECTING CONTACT WITH ROTATING BODY

[75] Inventors: Hiroaki Asano, Okazaki; Yasuhiro Kobayashi, Anjo; Shigeo Hotta; Yoichi Yamakawa, both of Aichi; Akira Ito; Hirotaka Sugiura, both of Kariya, all of Japan

[73] Assignee: Toyoda Koki Kabushiki Kaisha, Kariya, Japan

[21] Appl. No.: 125,752

[22] Filed: Sep. 24, 1993

[30] Foreign Application Priority Data

| Sep. 25, 1992 | [JP] | Japan | 4-279231 |
| Sep. 30, 1992 | [JP] | Japan | 4-261630 |
| Sep. 30, 1992 | [JP] | Japan | 4-261631 |
| May 31, 1993 | [JP] | Japan | 5-154241 |
| May 31, 1993 | [JP] | Japan | 5-154242 |

[51] Int. Cl.$^6$ .................................................. G01M 7/00
[52] U.S. Cl. ............................... 73/660; 73/587; 73/661
[58] Field of Search ............................ 73/587, 660, 661, 73/658

[56] References Cited

U.S. PATENT DOCUMENTS

| 4,617,503 | 10/1986 | Davis et al. | 318/572 |
| 4,631,683 | 12/1986 | Thomas et al. | 73/660 |
| 4,704,693 | 11/1987 | Thomas | 73/660 |
| 4,724,524 | 2/1988 | Thomas et al. | 73/660 |
| 4,782,452 | 11/1988 | Thomas | 73/660 |
| 4,821,460 | 4/1989 | Wegmann | 73/660 |
| 4,847,556 | 7/1989 | Langley | 73/660 |
| 5,076,102 | 12/1991 | Sato et al. | 73/587 |
| 5,187,434 | 2/1993 | Ando | 73/660 |
| 5,257,531 | 11/1993 | Motosugi et al. | 73/660 |

FOREIGN PATENT DOCUMENTS 4-63678  2/1992  Japan .

Primary Examiner—Richard Chilcot
Assistant Examiner—Eric S. McCall
Attorney, Agent, or Firm—Oblon, Spivak, McClelland, Maier & Neustadt

[57] ABSTRACT

An apparatus for detecting contact between a contact detection member and a rotating body such as a grinding wheel rotably carried on a wheel head which is movable toward the contact detection member in a grinding machine for example. The apparatus comprises an AE sensor, a rectangular pulse generator, a sampling circuit and a processing device such as a microcomputer. The AE sensor generates an electric signal in response to vibration of the contact detection member. The rectangular pulse generator outputs a rectangular pulse whose duration corresponds to that of vibration. The sampling circuit delivers to the processing device an output indicating the duration of the rectangular pulse. The processing device processes the output delivered thereto so as to decide the occurrence of an actual contact between the rotating body and the contact detection member.

7 Claims, 18 Drawing Sheets

SRPM

| BIT | ADDRESS | 1 | 2 | 3 | 4 | 5 | 6 | 7 | 8 | 9 | 10 | | N |
|---|---|---|---|---|---|---|---|---|---|---|---|---|---|
| 1 | | 0 | 1 | 0 | 1 | 1 | 1 | 1 | 1 | 1 | 0 | | 0 |
| 2 | | 1 | 0 | 1 | 1 | 1 | 1 | 1 | 1 | 1 | 0 | | 0 |
| 3 | | 0 | 1 | 0 | 0 | 1 | 1 | 1 | 0 | 1 | 0 | | 1 |
| ⋮ | | ⋮ | ⋮ | ⋮ | ⋮ | ⋮ | ⋮ | ⋮ | ⋮ | ⋮ | ⋮ | | ⋮ |
| n | | 1 | 0 | 0 | 0 | 0 | 1 | 1 | 0 | 0 | 1 | | 1 |

*FIG. 9*

SMA

| ADDRESS | 1 | 2 | 3 | 4 | 5 | 6 | 7 | 8 | 9 | 10 | | N |
|---|---|---|---|---|---|---|---|---|---|---|---|---|
| BIT STATUS | 0 | 0 | 0 | 0 | 0 | 1 | 1 | 0 | 0 | 0 | | 0 |

*FIG. 11*

APPARATUS FOR DETECTING CONTACT WITH ROTATING BODY

BACKGROUND OF THE INVENTION

1. Field of the Invention

The present invention relates to an apparatus for detecting the contact with a rotating body. More particularly, it relates to an apparatus for detecting the contact between a contact detection member and an outer peripheral surface of a rotating grinding wheel.

2. Discussion of the Prior Art

In a grinding machine, an apparatus for detecting the position of an outer peripheral surface of a rotating grinding wheel prior to truing the grinding surface or grinding a workpiece, uses a contact detection member which is fixed to a head stock on a work table and which incorporates an acoustic emission sensor (AE sensor). A wheel head with a grinding wheel is moved toward the contact detection member and the position of the grinding surface is detected when the grinding surface touches with the contact detection member at which time the AE sensor detects sound wave which is exerted on the detection member. The contact with the grinding wheel is decided based upon the level of a signal output from the AE sensor, and the surface position of the wheel is obtained by reference to the amount of forward feed of the wheel head when the grinding surface is decided as having contacted with the contact detection member.

This apparatus has, however, the following drawback:

For a similar condition to an actual truing or grinding operation, coolant is ejected from a nozzle during such contact detection operation and adversely acts on the contact detection member. The AE sensor detects shocks caused by coolant and outputs an electric signal. As a result, the contact detection apparatus may decide as the contact having been made, in response to the output signal which the AE sensor issues though the grinding surface has actually not touched with the contact detection member.

SUMMARY OF THE INVENTION

It is, therefore, a primary object of the present invention to provide an apparatus capable of precisely detecting the contact between a contact detection member and a rotating body.

Another object of the present invention is to provide a contact detection apparatus which is capable of precisely and reliably deciding the contact between a contact detection member and an outer peripheral surface of a rotating body such as, preferably a grinding wheel, without being influenced by disturbances such as coolant colliding against the contact detection member.

A further object of the present invention is to provide a contact detection member particularly designed for precisely detecting such contact.

Briefly, a contact detection apparatus according to the present invention comprises a contact detection member for detecting a position of a rotating body through the contact therewith, a sensor for generating an electrical signal upon a contact of the detection member with the rotating body at each of plural rotations of the same, rectangular pulse generating means responsive to the electrical signal for generating a rectangular pulse whose duration corresponds to the time period of a contact made between the detection member and the rotating body, sampling means responsive to the rectangular pulse for delivering an output propotional to the duration of the rectangular pulse, and processing means responsive to the output for processing the same so as to discriminate an actual contact of the detection member with the rotating body, from disturbance acting on the detection member.

With this configuration, because the output which is delivered to the processing means upon an actual contact between the rotating body and the detection member occurs with the rotating body being at least one same angular position throughout plural rotations of the rotating body or is relatively long compared with that caused by disturbances, such actual contact can be detected precisely and reliably.

In another aspect of the present invention, the output delivered to the processing means is stored in a memory means in connection with the angular position of the rotating body. The storage of the output is carried out with respect to each of different angular positions of the rotating body and each of predetermined number of rotations of the rotating body. This causes the memory means to store contact signals at least one same address, so that an actual contact of the detection member with the rotating body can be detected reliably since disturbances do not result in storing the contact signals at the same address of the memory means.

In still another aspect of the invention, at each rotation of the rotating body, a contact detection signal is memorized if the same was detected at the same angular position or the next in either direction thereto in the preceding rotation of the rotating body. Thus, even if the contact signals are detected at somewhat different angular positions of the rotating body during plural rotations of the same, such detected contact signals are regarded as resulting from an actual contact at the same angular position, so that a slight fluctuation can be permitted in the rotational speed of the rotating body, thereby not requiring that a motor for driving the rotating body be of a high quality.

In a further aspect of the invention, when contact signals are detected at two or more successive angular positions of the rotating body throughout plural rotations of the same, an actual contact of the rotating body with the detection member is decided to have occurred. This makes it possible to more accurately detect such actual contact without suffering disturbance.

In an additional aspect of the invention, data indicating the duration of a contact signal is memorized in connection with each of different angular positions of the rotating body, which makes it possible to reliably discriminate an actual contact between the rotating body and the detection member from disturbance.

In a still further aspect of the invention, the detection member takes the form of a hollow pipe, so that the influence caused by disturbance can be diminished, thereby realizing the precise and reliable detection of an actual contact between the rotating body and the detection member.

BRIEF DESCRIPTION OF THE ACCOMPANYING DRAWINGS

Various other objects, features and many of the attendant advantages of the present invention will be readily appreciated as the same becomes better understood by reference to the following detailed description of the preferred embodiments when considered in connection with the accompanying drawings, in which.

Figure 1:
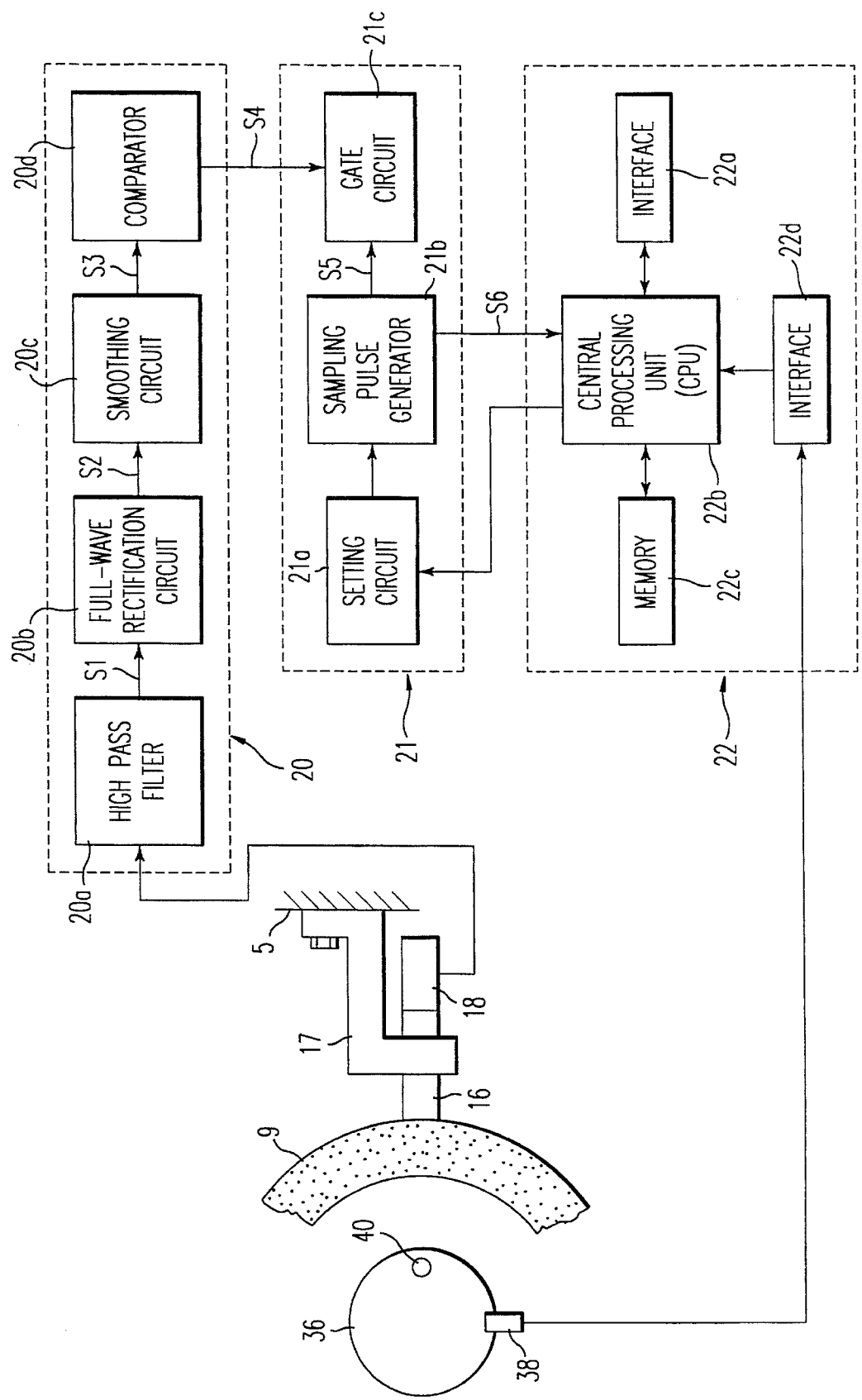
FIG. 1 is a partial view as viewed in the direction of the allow A in FIG. 2, also incorporating a block diagram of an electrical system for a contact detection apparatus of a first embodiment according to the present invention.
Figure 3A:
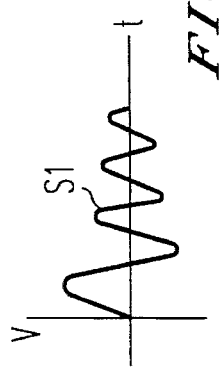
Figure 3B:
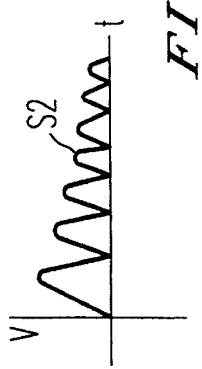
Figure 3C:
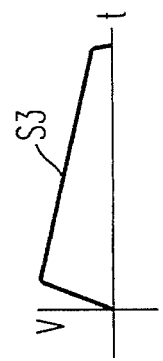
Figure 3D:
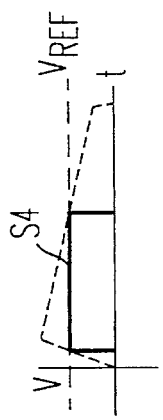
Figure 4:
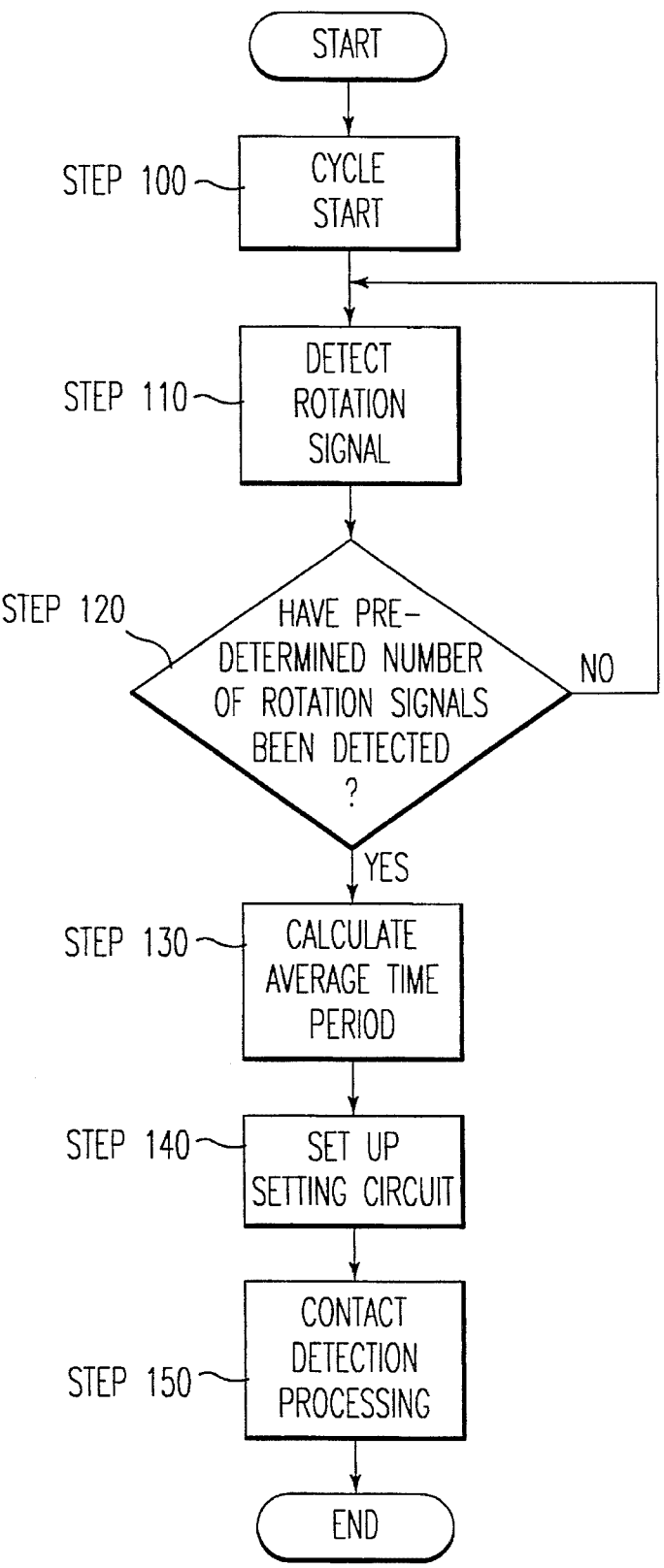
Figure 5A:
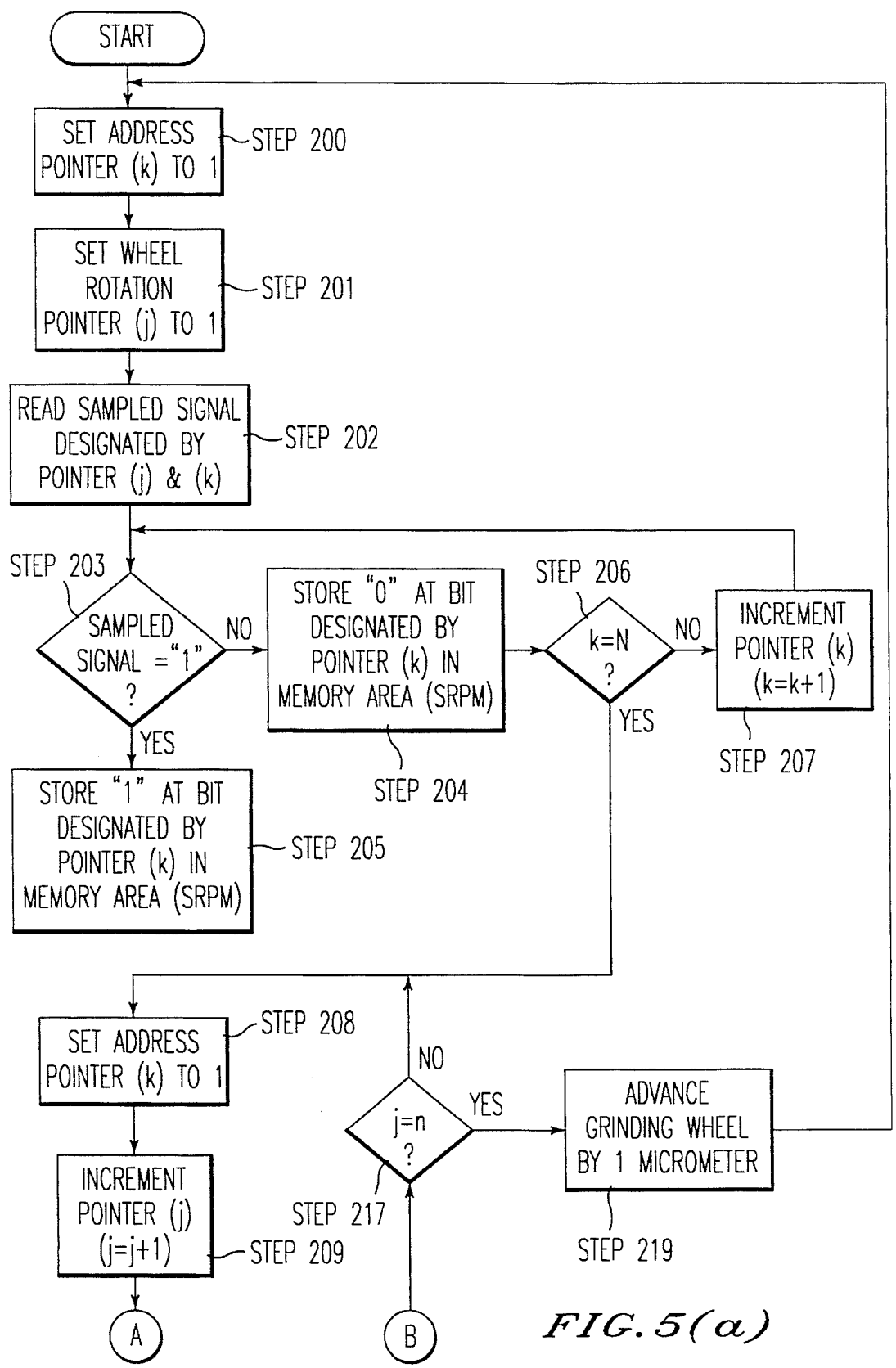
Figure 5B:
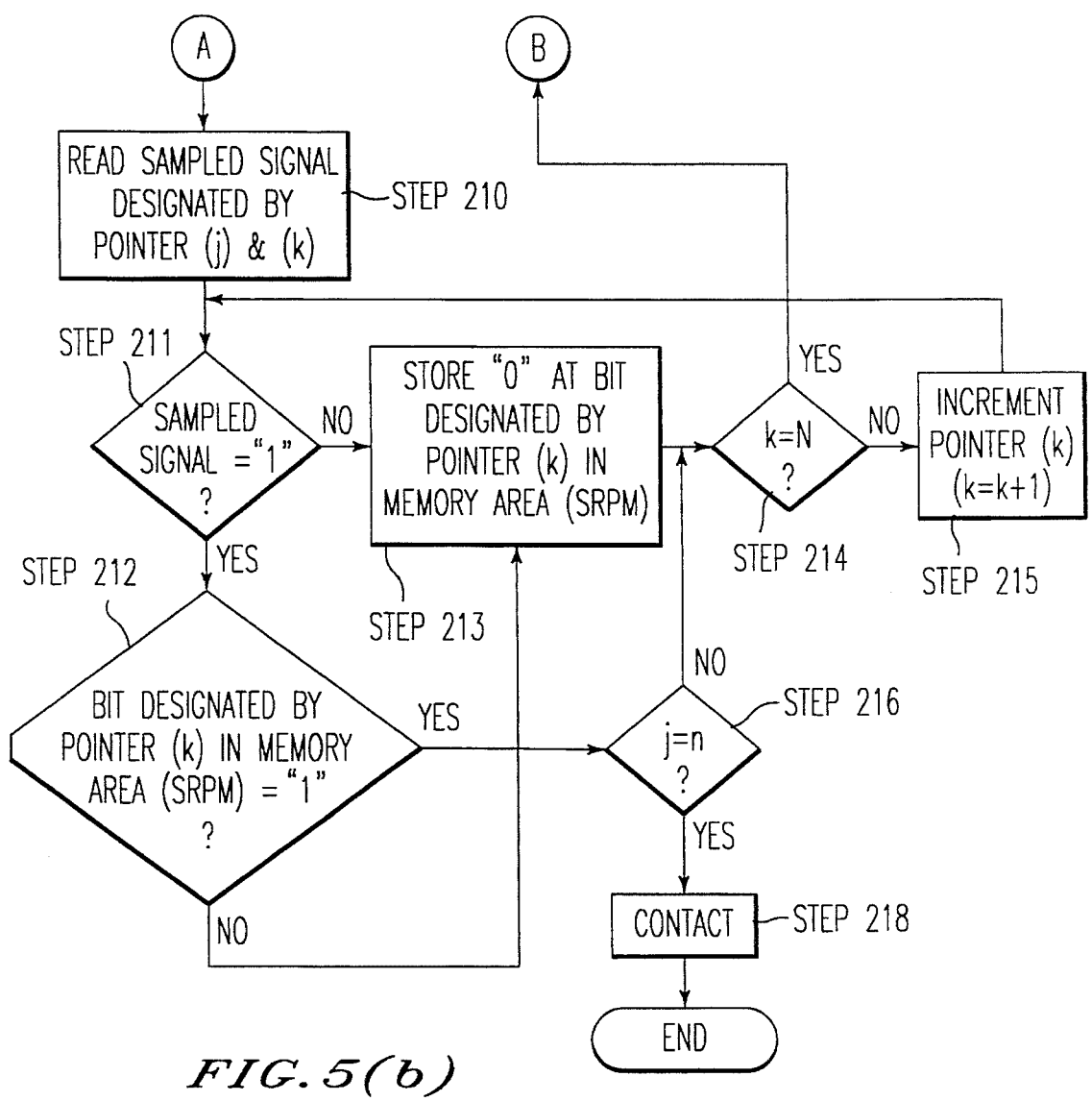
Figure 6:
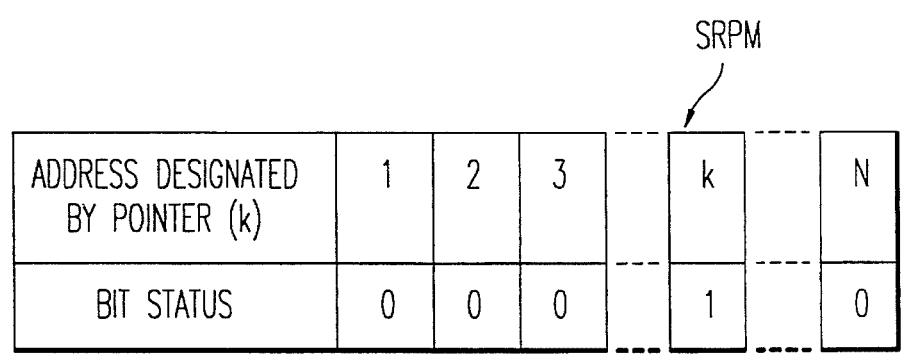
Figure 7:
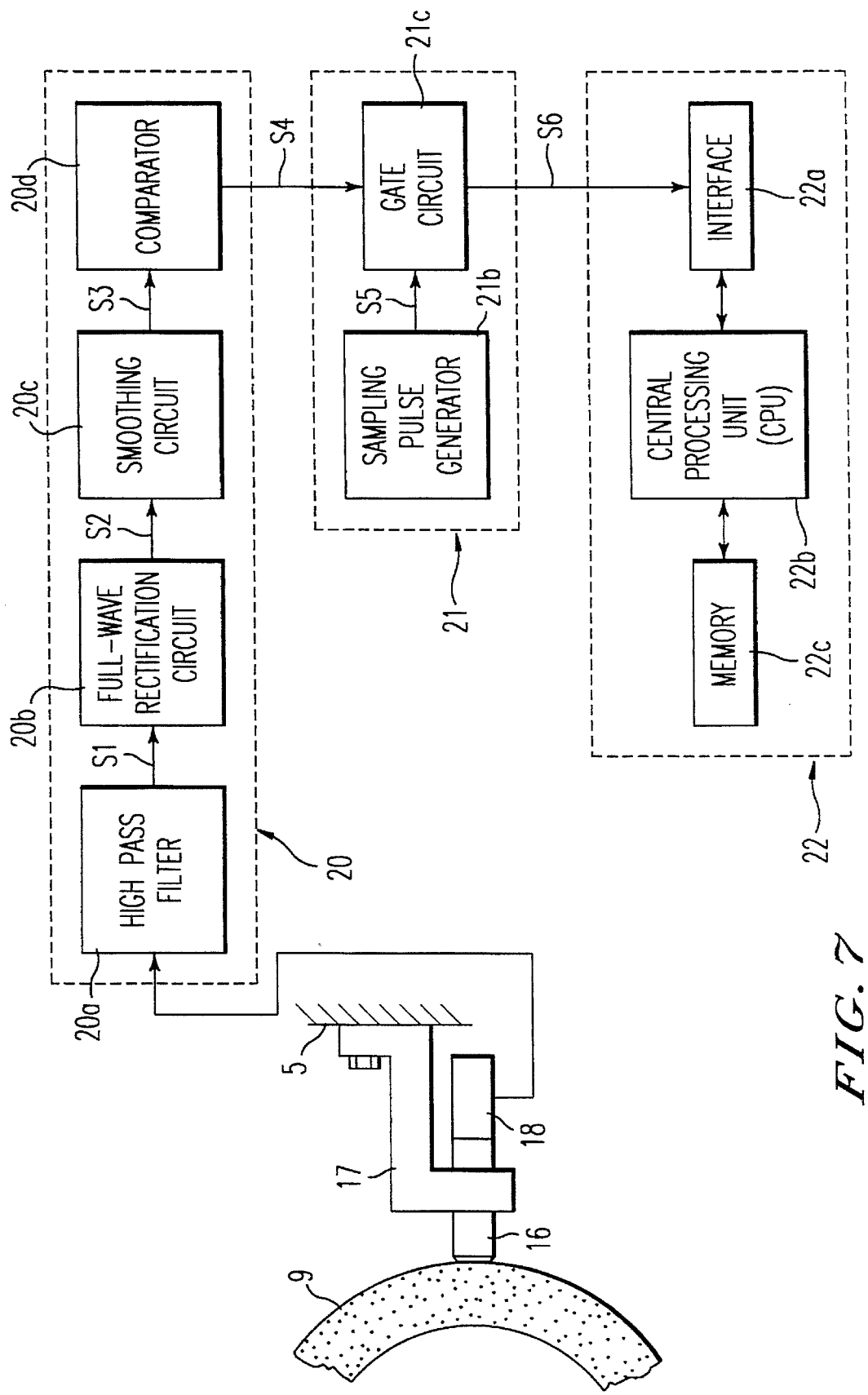
Figure 8:
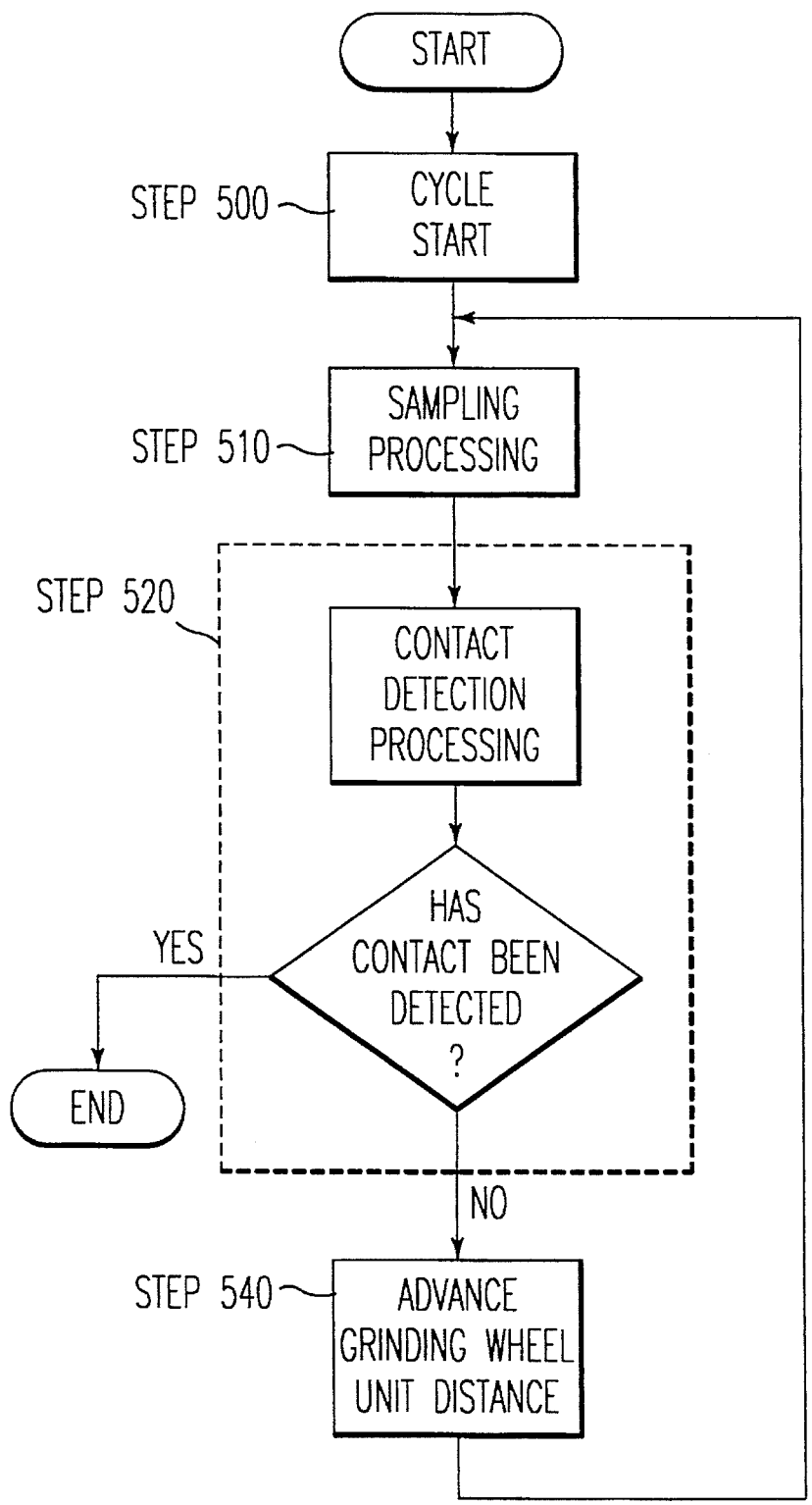
Figure 10A:
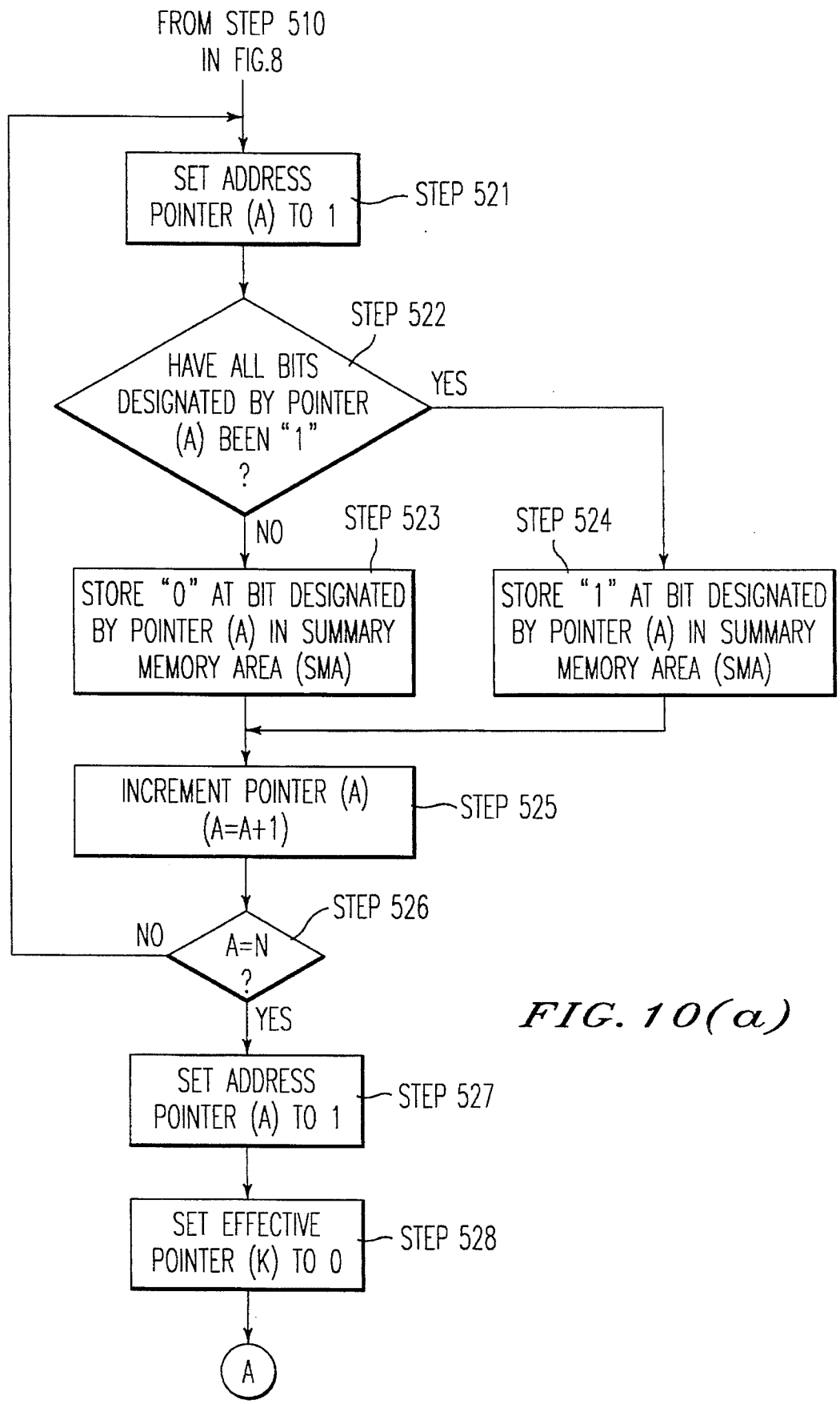
Figure 10B:
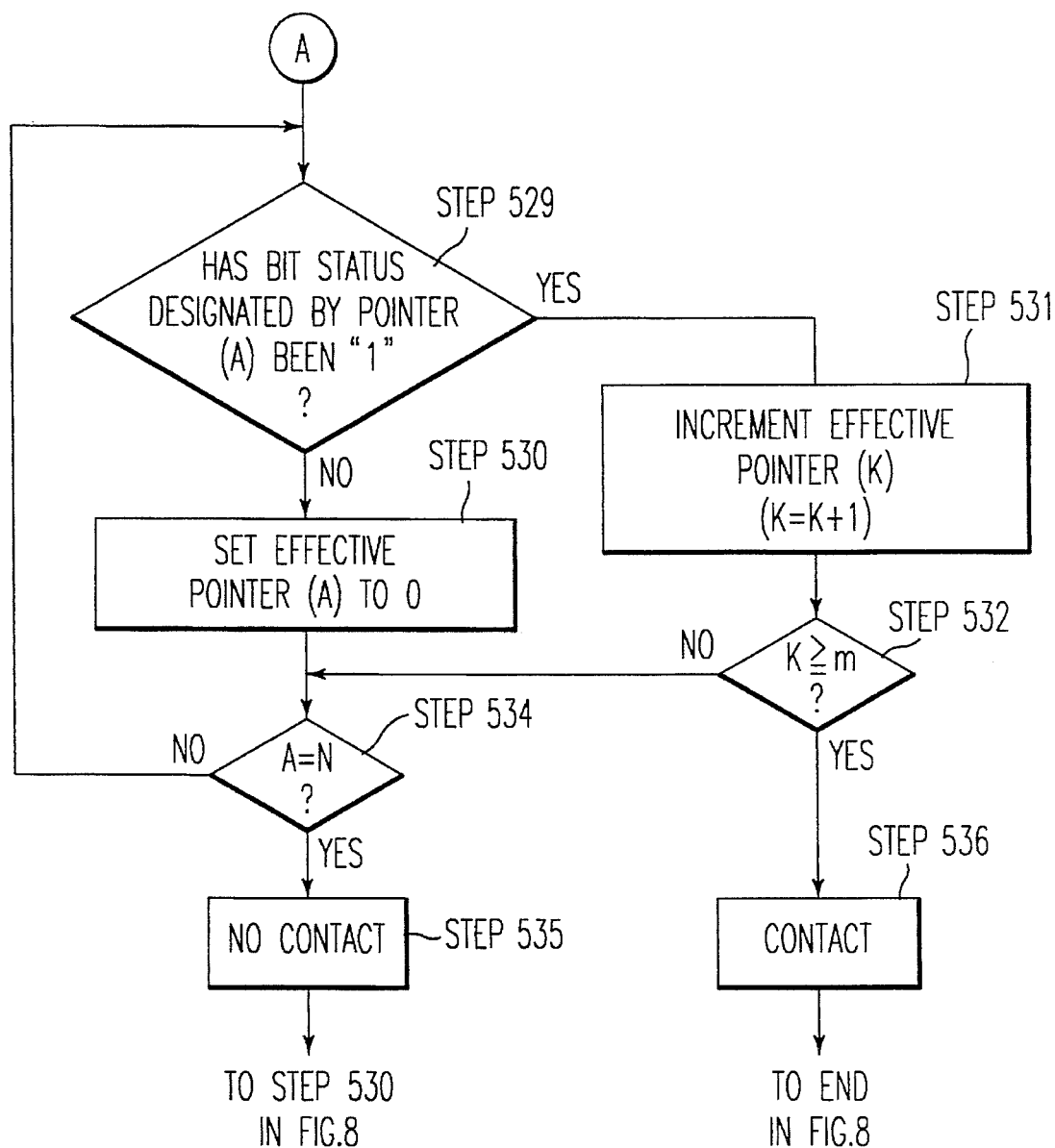
Figure 12A:
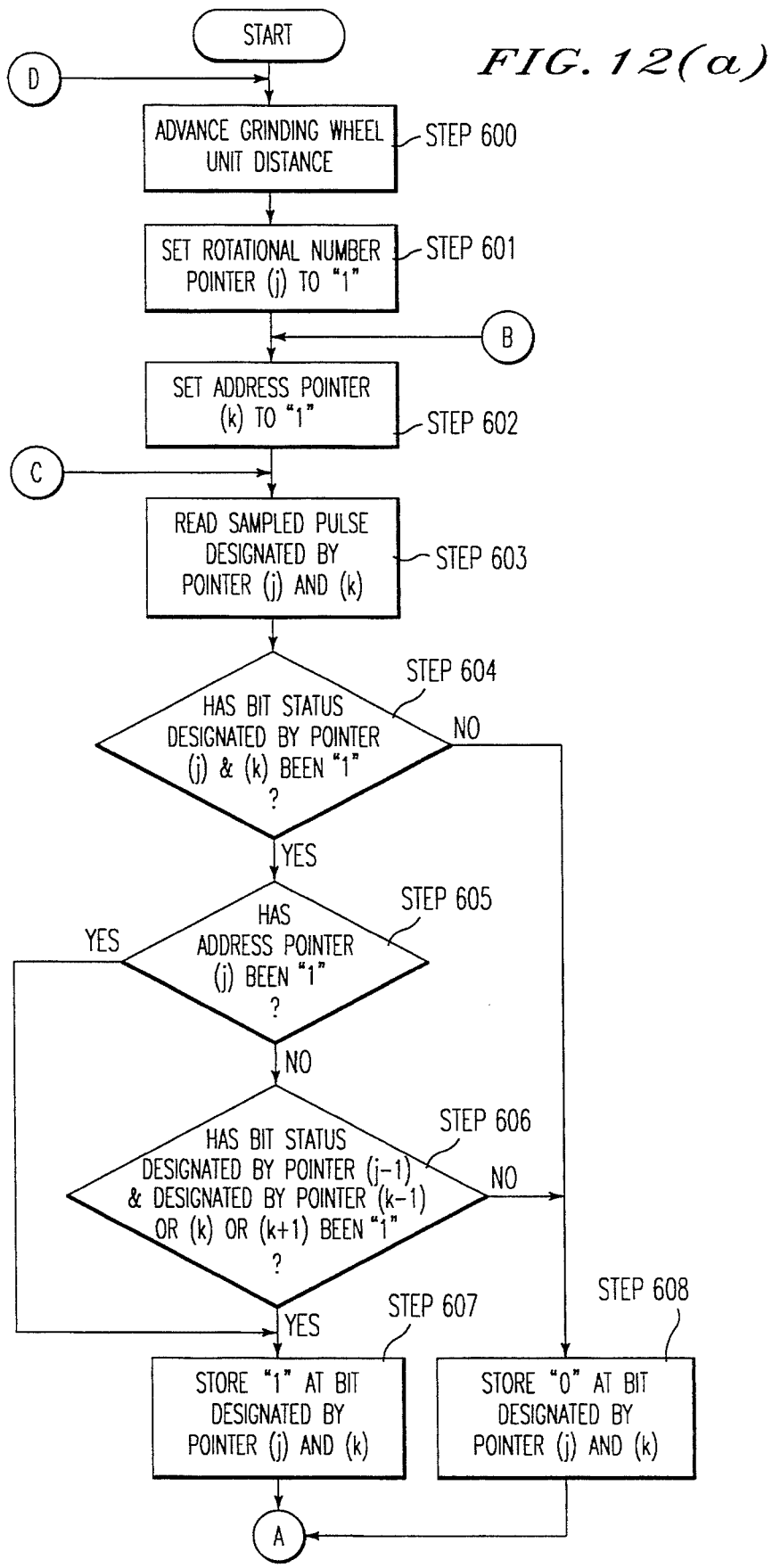
Figures 12B, 13:
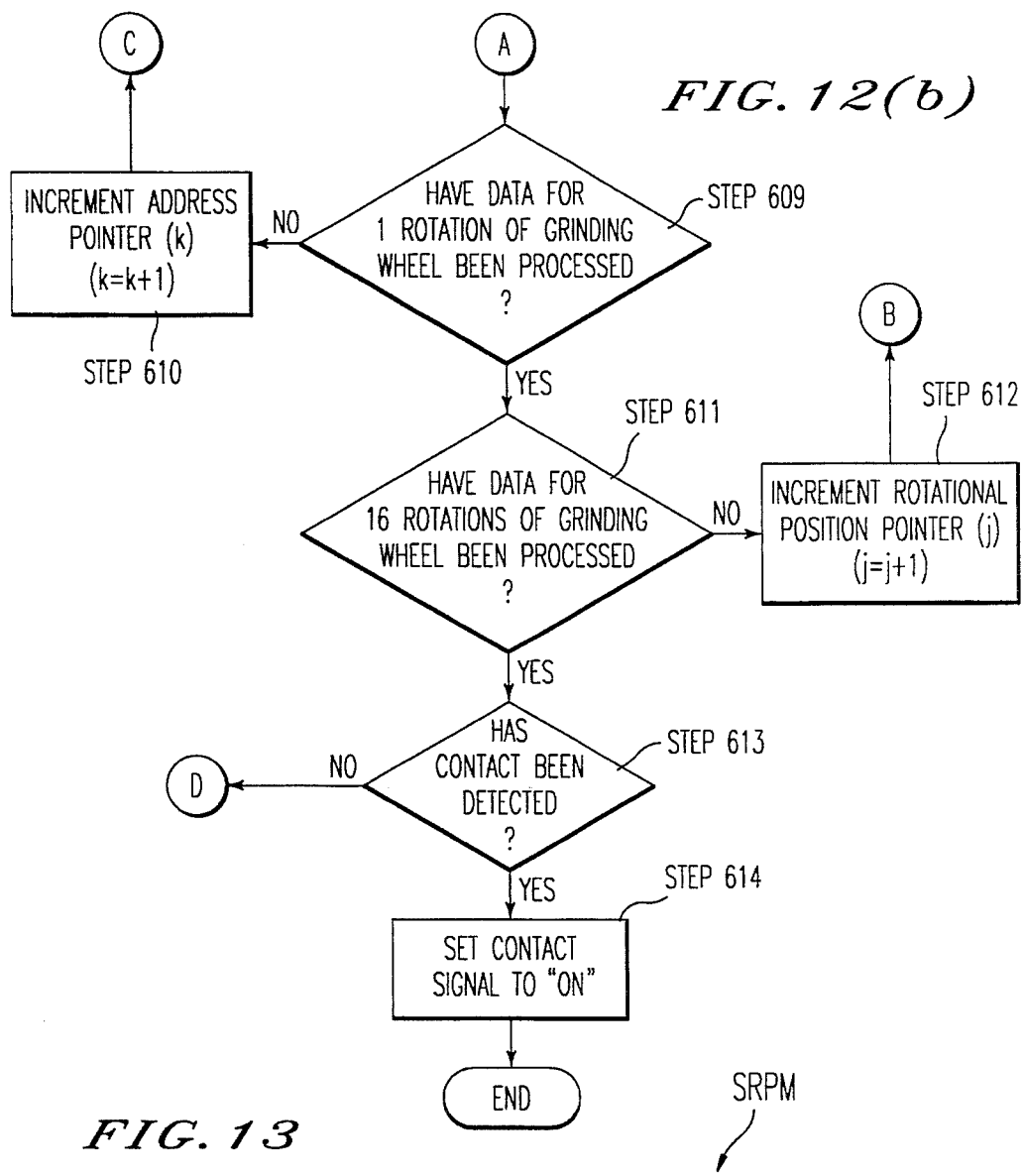
Figure 14A:
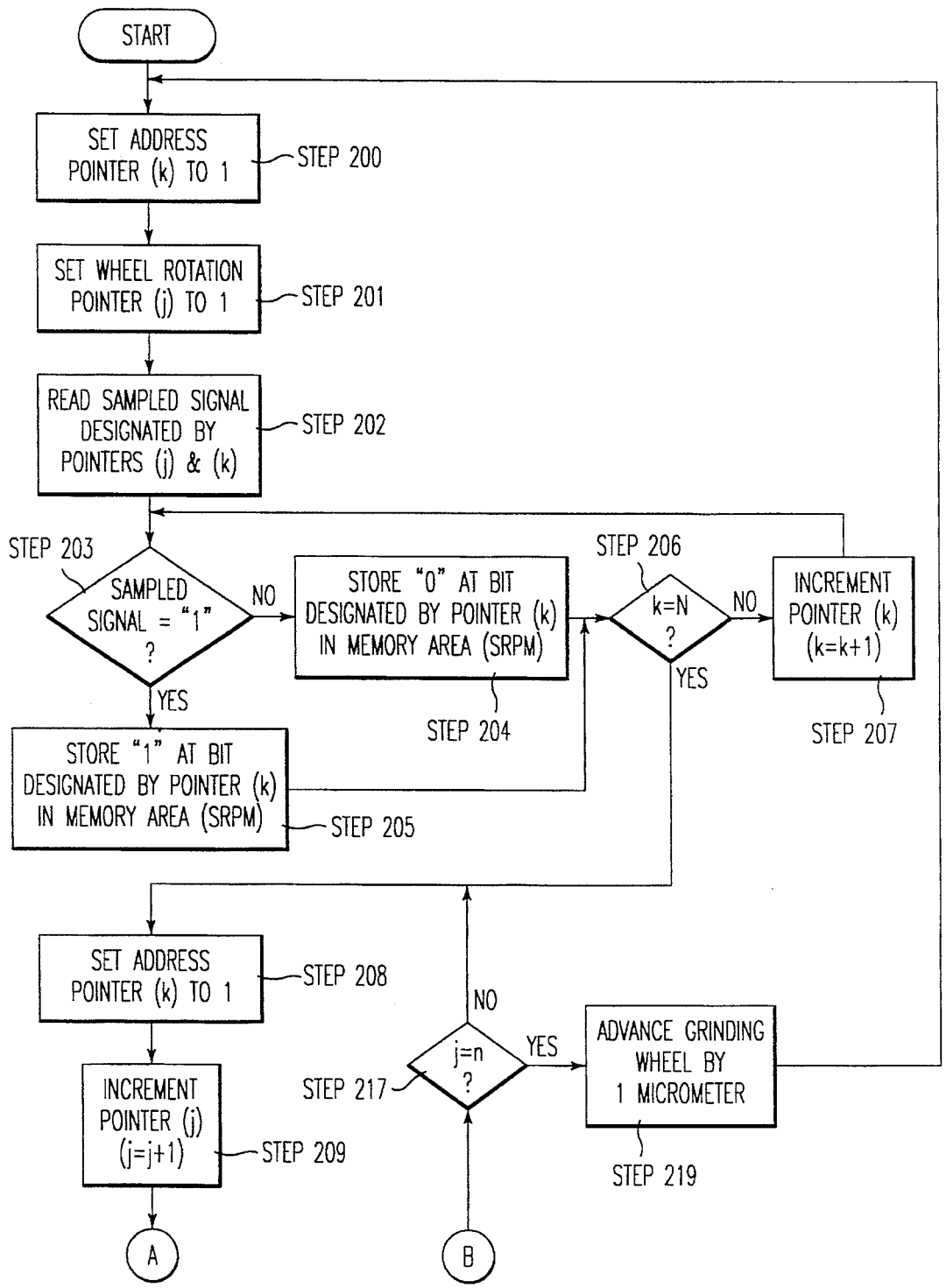
Figure 14B:
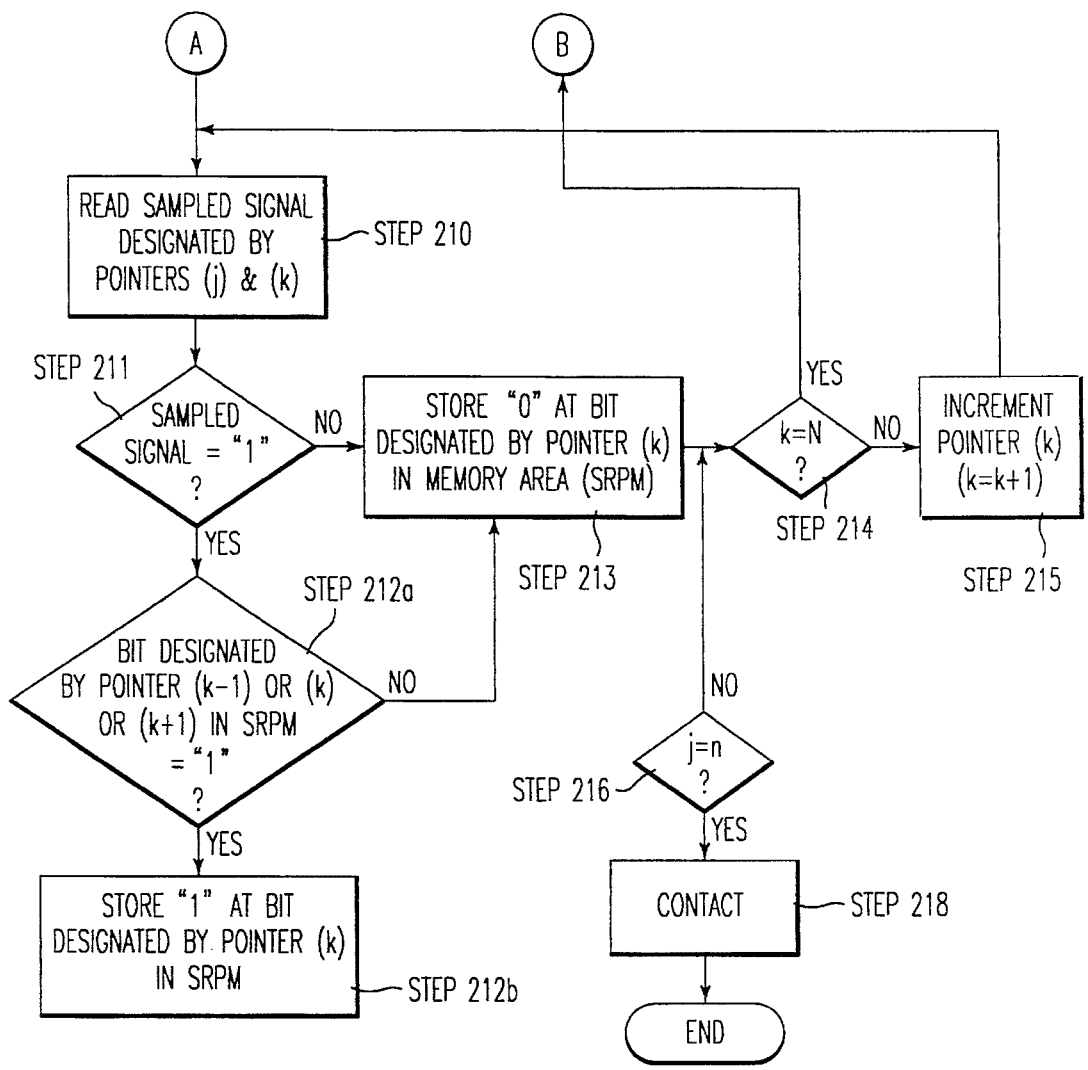
Figure 15:
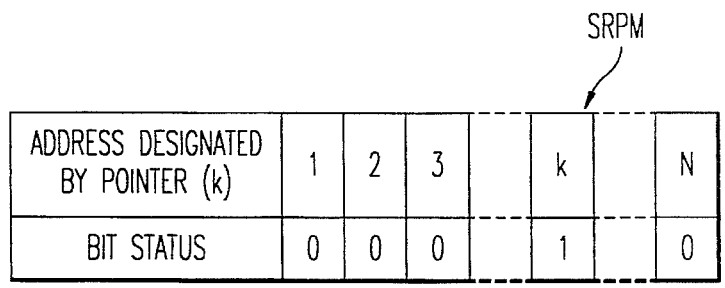
Figure 16:
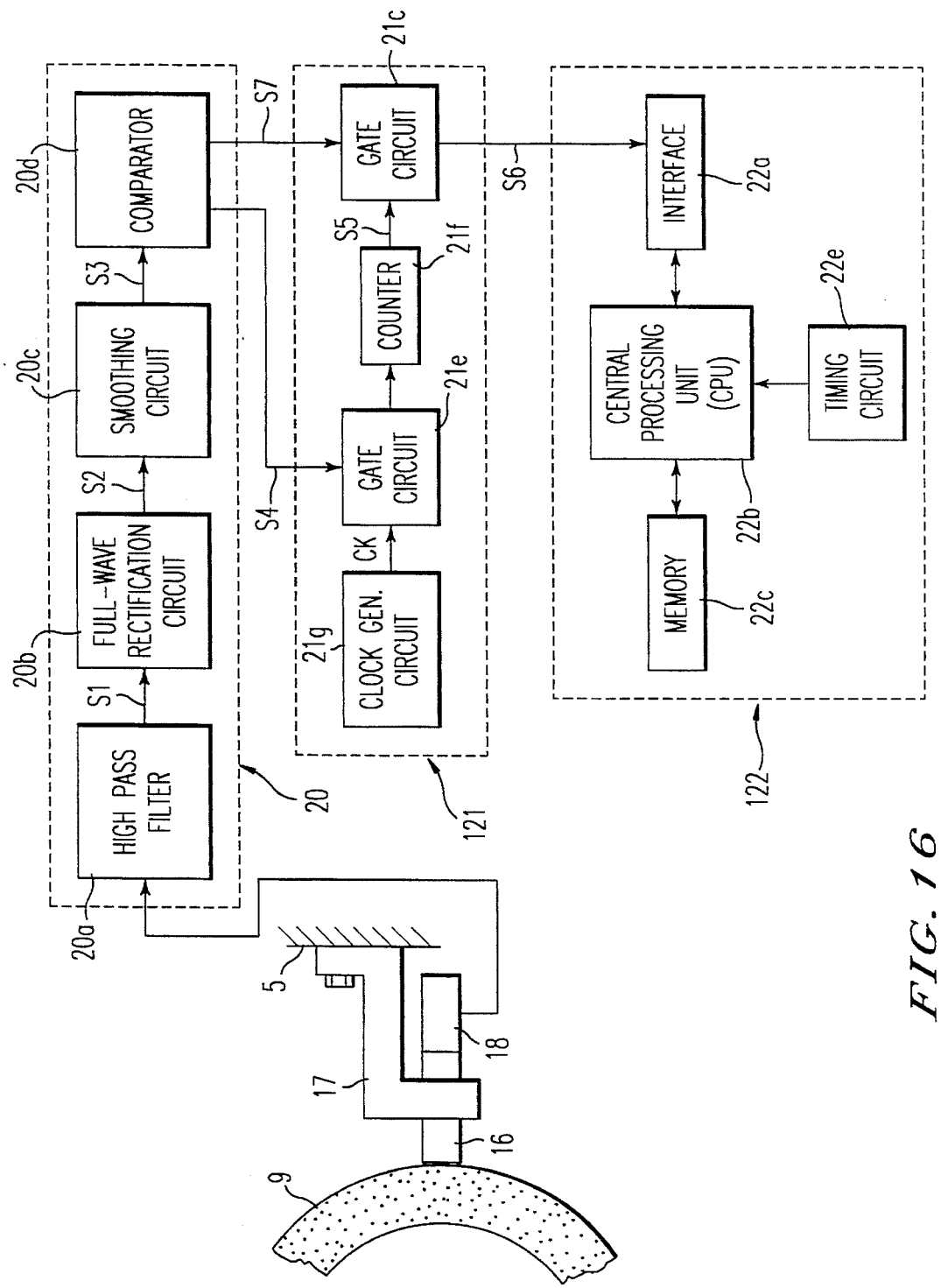
Figure 17:
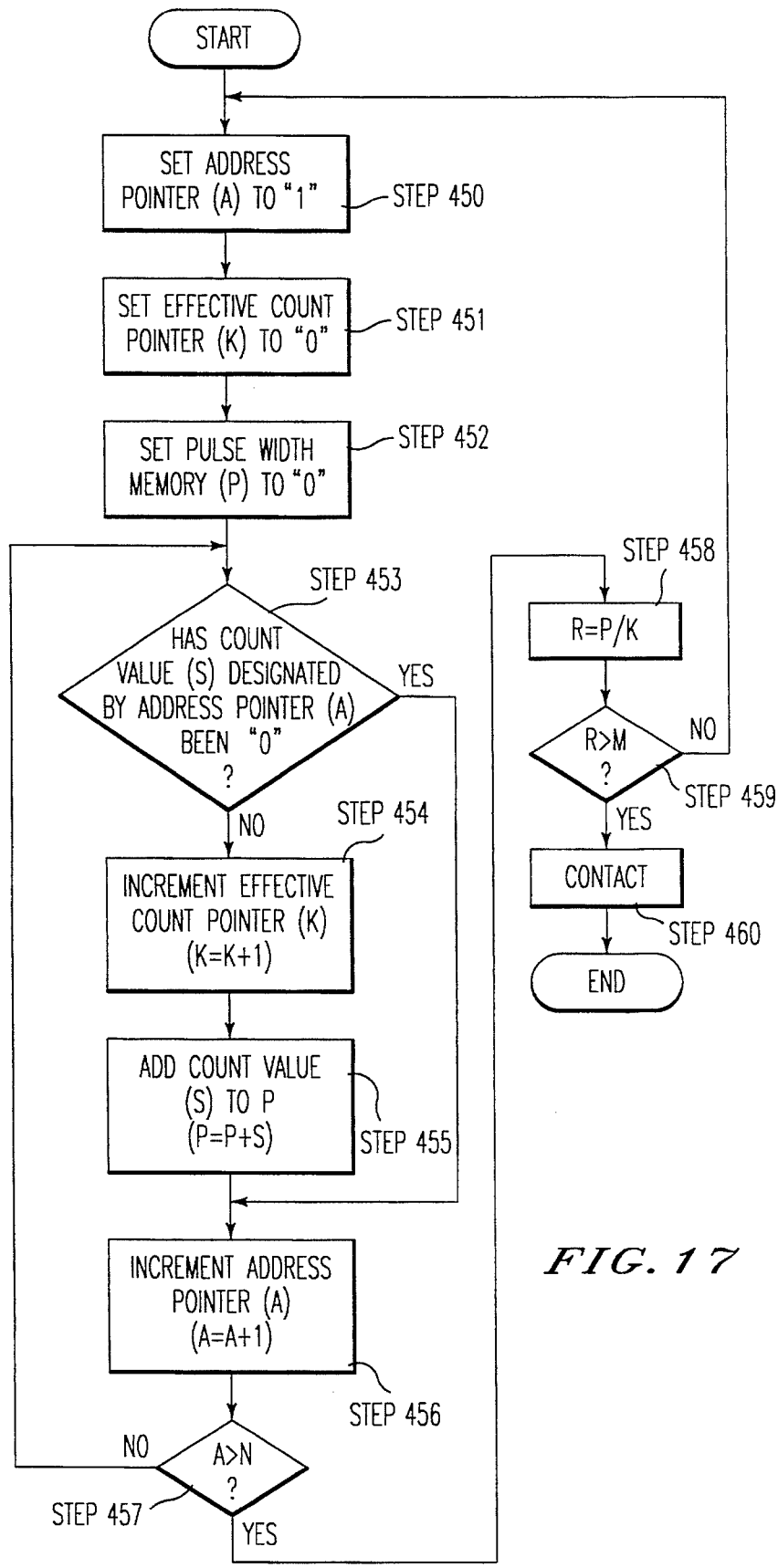
Figures 18, 19:
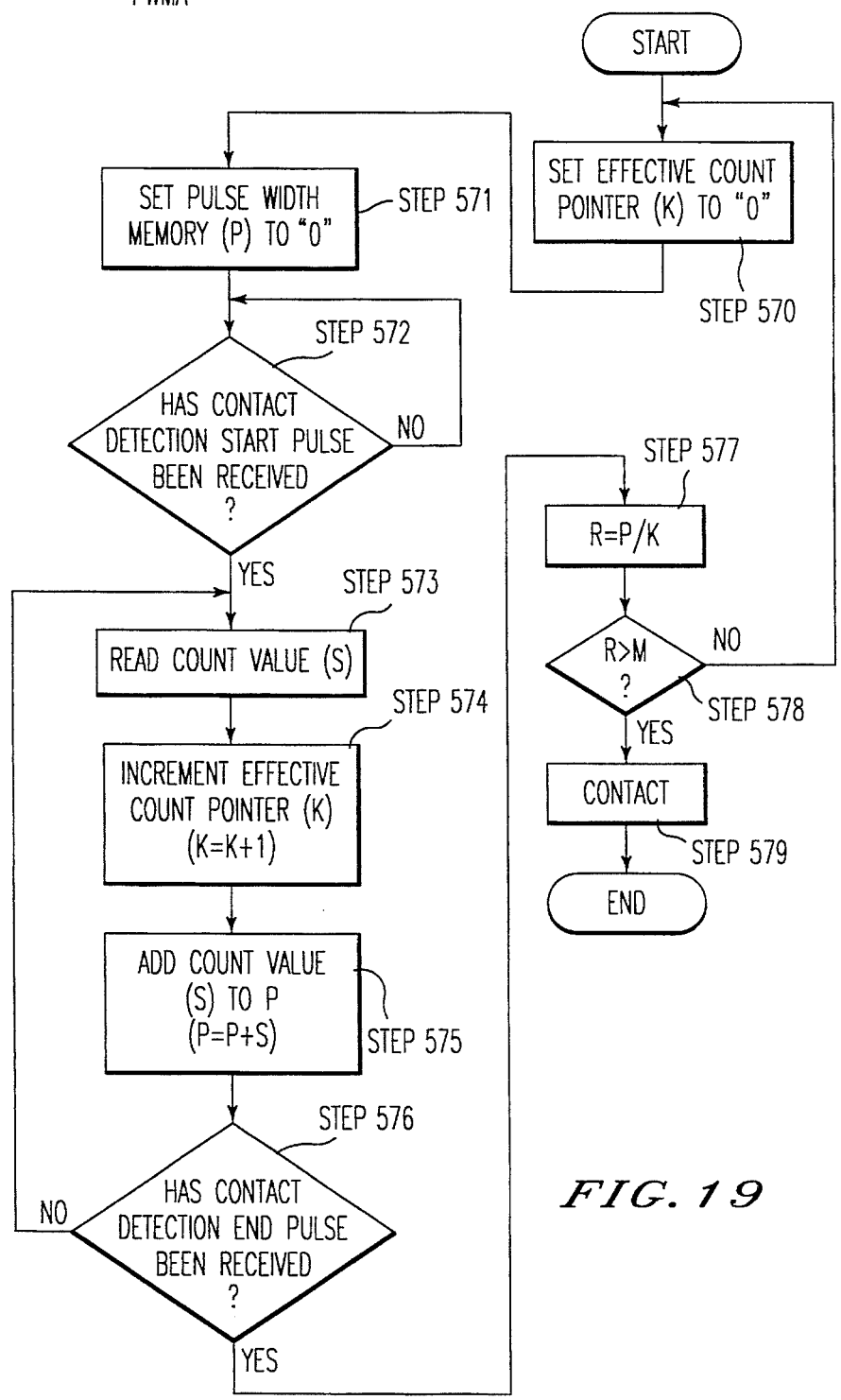
Figure 20:
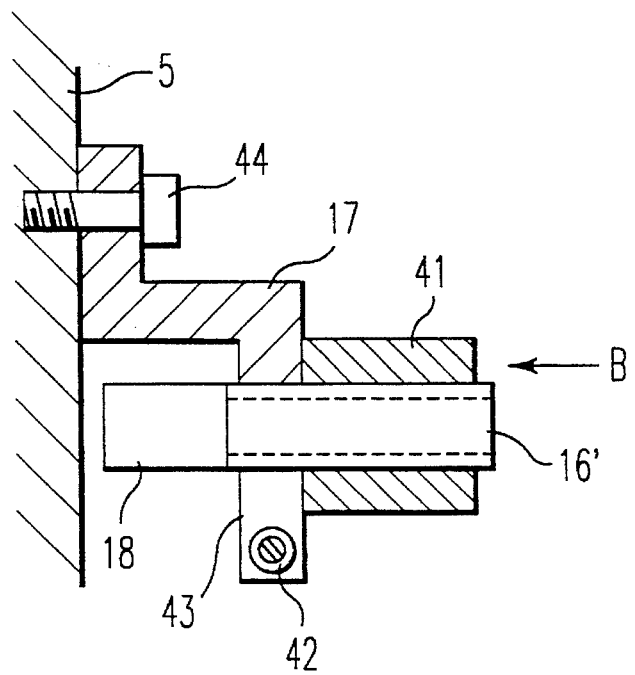
Figure 21:
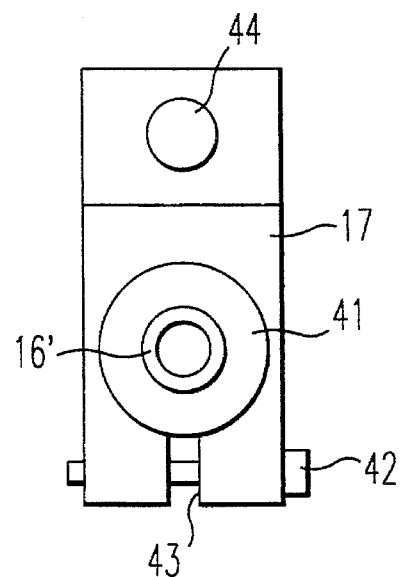

FIGS. 3(a) through 3(d) are graphs showing the progress in processing a detected sound wave;

FIG. 4 is a flow chart showing a general processing of a CPU used in the first embodiment;

FIGS. 5(a) and 5(b) show another flow chart executed by the CPU in the first embodiment of the present invention;

FIG. 6 shows a sampled rectangular pulse memory area for storing contact signals in the first embodiment;

FIG. 7 is a view similar to FIG. 1 used in a second embodiment of the present invention;

FIG. 8 is a flow chart for CPU's general processing executed in the second embodiment;

FIG. 9 shows a sampled rectangular pulse memory area for storing contact signals in the second embodiment;

FIGS. 10(a) and 10(b) show a flow chart executed by the CPU in the second embodiment;

FIG. 11 shows a summary memory area for storing the summarized results of contact judgement in the second embodiment;

FIGS. 12(a) and 12(b) show a processing executed by the CPU in a third embodiment of the present invention;

FIG. 13 shows a sampled rectangular pulse memory area for storing contact signals in the third embodiment;

FIGS. 14(a) and 14(b) show CPU's processing used in place of that shown in FIGS. 12(a) and 12(b) in a modification of the third embodiment;

FIG. 15 is a summary memory area used in the modification of the third embodiment;

FIG. 16 is a view similar to FIG. 1 but used in a fourth embodiment of the present invention;

FIG. 17 is a flow chart showing a processing executed by the CPU in the fourth embodiment;

FIG. 18 shows a pulse width memory area for storing contact durations at different angular positions of a grinding wheel in the fourth embodiment;

FIG. 19 is a flow chart corresponding to FIG. 17 and used in a modification of the fourth embodiment;

FIG. 20 is a fragmentary sectional view of a contact detection member used in a fifth embodiment of the present invention; and FIG. 21 is a front view of the contact detection member as viewed from the arrow B in FIG. 20.

DETAILED DESCRIPTION OF THE PREFERRED EMBODIMENTS (First Embodiment)

Figure 2:
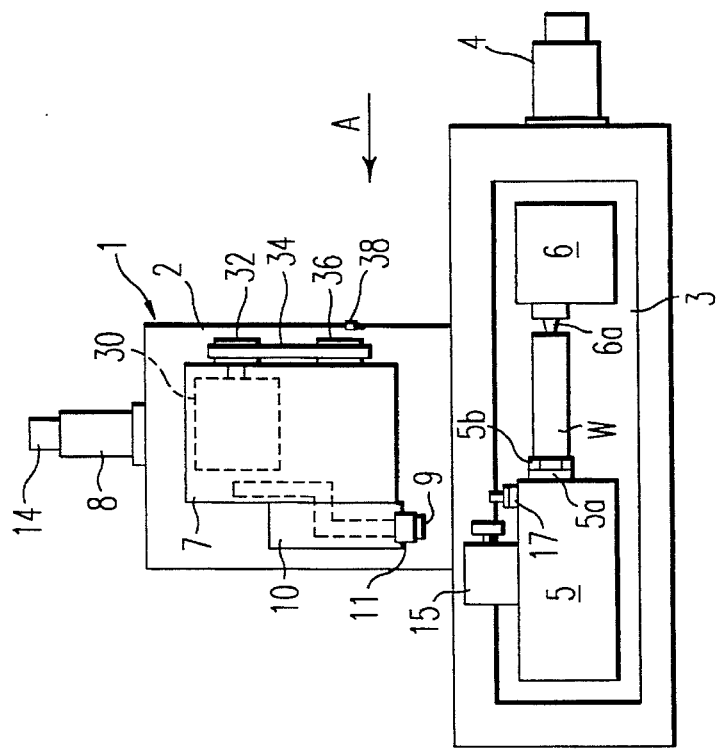
FIG. 2 is a top plan view of a grinding machine having the contact detection apparatus.

Referring to FIG. 2 of the drawings, there is shown a grinding machine 1 incorporating a contact detection apparatus of the first embodiment according to the present invention.

The grinding machine 1 has a bed 2. A work table 3 is arranged on the bed 2 and is movable by a ball screw (not shown) in a first direction parallel to the rotational axis of a workpiece W. The ball screw is rotated by a servomotor 4. A head stock 5 and a tailstock 6 are arranged on the work table 3. The head stock 5 has a chuck 5a, while the tailstock 6 has a center 6a. The workpiece W is rotatable between the chuck 5a and the center 6a.

A wheel head 7 is arranged on the bed 2 and is movable by a ball screw (not shown) which is in turn rotated by a servomotor 8, in a second direction perpendicular to the first direction. A grinding wheel 9 covered by a wheel cover 10 is arranged on the wheel head 7 for grinding the workpiece W. A coolant nozzle 11 is provided on the wheel head 7 and is joined to a coolant pipe 12. Coolant is supplied to the machining point from the nozzle 11 through the coolant pipe 12.

An encoder 14 detects the number of rotations of the servomotor 8 and a numerical control unit (not shown) calculates amount of movement of the wheel head 7 on the basis of the number of rotations. A truing apparatus 15 is fixed to the head stock 5 at a position facing the grinding wheel 9. A contact detection member 16 for detecting an outer peripheral position of the grinding wheel 9 is fixed to the head stock 5 by a support member 17 to face the wheel head 7. An AE (acoustic emission) sensor 18 is secured to the rear end of the contact detection member 16 for detecting a sound wave which occurs either when the outer peripheral grinding surface of the grinding wheel 9 touches with the contact detection member 16 or when coolant hits the same, so as to convert the detected sound wave into an electric signal.

The grinding wheel 9 and an invertermotor 30 are coupled by two pulleys 32, 36 and a belt 34, so that the grinding wheel 9 is rotatable by the invertermotor 30.

Referring to FIGS. 1 and 3 of the drawings, there is shown a contact detection apparatus used in the first embodiment of the present invention, being composed of a rectangular pulse generating circuit 20, a sampling circuit 21 and a signal processing circuit 22.

The rectangular pulse generating circuit 20 is provided for rectifying a sound wave which is detected by the AE sensor 18 and which is above a predetermined level and for outputting a rectangular pulse which corresponds to the sound wave in duration. The circuit 20 comprises a high pass filter 20a, a full-wave rectification circuit 20b, a smoothing circuit 20c and a comparator 20d. The high pass filter 20a removes a mechanical vibration component from the electric signal detected by the AE sensor 18 to output an electric signal S1. The full-wave rectification circuit 20b rectifies the electric signal S1 to output a rectified signal S2. The smoothing circuit 20c smooths the rectified signal S2 to output a smoothed signal S3. The comparator 20d compares the smoothed signal S3 with a reference signal $V_{ref}$ and outputs a rectangular pulse S4 whose level is maintained high while the smoothed signal S3 exceeds the reference signal level $V_{ref}$.

The sampling circuit 21 comprises a setting circuit 21a, a sampling pulse generator 21b and a gate circuit 21c. The setting circuit 21a sets up sampling time intervals on the basis of a time period taken for the grinding wheel 9 or the pulley 36 to complete one-full rotation. The sampling pulse generator 21b generates plural sampling pulses S5 corresponding to the sampling time intervals. The gate circuit 21c opens its gate in response to each rectangular pulse S4 and outputs sampled rectangular pulses S6 to which the pulses S4 and S5 are ANDed.

The signal processing circuit 22 comprises first and second interfaces 22a, 22d, a memory 22c and a CPU 22b. The first interface 22a receives the sampled rectangular pulses S6 and sends the same for storage in the memory 22c. A signal "1" or "0" is stored in the memory 22c when each sampled rectangular pulse S6 is high or low, respectively. FIG. 6 shows a sampled rectangular pulse memory area SRPM in the memory 22c for storing the sampled rectangular pulse signals "1" or "0". This area SRPM has a predetermined number N (N=128 in this particular embodiment) of addresses. The second interface 22d receives a rotational signal detected by a rotational sensor 38 for use in calculating the time period for each rotation of the grinding wheel 9.

A member 40 like a pin is arranged on the pulley 36 and the rotational sensor 38 generates a rotational signal each time the member 40 passes by the rotational sensor 38. Therefore, the time period per one rotation of the grinding wheel 9 or the pulley 36 is obtained by measuring a time interval between a certain rotational signal and the next one.

The CPU 22b operates for two functions.

As the first function, it calculates a sampling time interval on the basis of the time interval between a rotational signal and the next one which are detected by the rotational sensor 38. The calculated sampling time interval is output to the setting circuit 21a.

As the second function, it determines whether the grinding wheel 9 has contacted with the contact detection member 16 or not, on the basis of data stored in the memory 22c.

The operation of the apparatus as constructed above will be described hereafter. Referring to FIG. 4 showing the entire processing executed by the CPU 22b, a cycle start at step 100 causes the wheel head 7 to move to a contact detection start position where the grinding wheel 9 is brought into slight ahead of the contact detection member 16. Step 110 involves detecting the rotational signal which is generated when the member 40 passes by the rotational sensor 38. At step 120, it is decided whether the CPU 22b has detected the rotational signal a predetermined number of times, (e.g., 5 times) or not. Step 130 is reached when decision is "YES" or step 110 is reached when decision is "NO". The CPU 22b counts its internal clocks from the time when it receives a first rotational signal until the time when it receives a sixth rotational signal, so as to calculates the time period for five rotations of the grinding wheel 9. Step 130 is for calculating an average time period per one rotation of the grinding wheel 9 on the basis of the calculated time period. Namely, the average time is obtained by dividing the calculated time period by five (5). A sampling time interval is then calculated by dividing the average time by a predetermined number, for example, 128 and is set to the setting circuit 21a. Processing then comes to step 150 when the setting circuit 21a finishes setting the sampling time. At step 150, decision is made as to whether the grinding wheel 9 is in contact with the contact detection member 16 or not, which will be described later in detail.

FIGS. 5(a) and 5(b) specifically show a decision processing at the aforementioned step 150.

An address pointer (k) and a wheel rotation pointer (j) are set to 1 at steps 200 and 201, respectively. A sampled rectangular pulse S6 from the first interface 22a is read at step 202 and is Judged to be "1", or "0" at step 203. If the sampled rectangular pulse S6 is "1", "1" is stored at the first address of the memory area SRPM designated the address pointer (k). If the sampled rectangular pulse S6 is "0", "0" is stored at the first address. Thereafter, it is Judged at step 206 whether or not the memory pointer (k) has reached the last memory address (N) of the memory area SRPM (i.e., 128th in this particular embodiment). Since (k) does not indicate (N) at this time, processing advances to step 206, wherein (k) is incremented before advancing to step 203.

Thus, until (k) becomes equal to (N), that is until the grinding wheel 9 completes one-full rotation, 128-sampled rectangular pulses are respectively stored at the address 1 to 128 of the memory area SRPM. The 128 sampled rectangular pulses each indicating "1" or "0" respectively correspond to the 128 angular positions of the grinding wheel 9. When k=N is answered at step 206, step 208 is reached to set k=1, and (j) is incremented to indicate the second rotation of the grinding wheel 9. A sampled rectangular pulse S6 is read at step 210 and is judged to be "1" or "0" at step 211. If the sampled rectangular pulse S6 is "1", the status of a signal being stored at the first address of the memory area SRPM is Judged to be "1" or "0". If the signal status at the first address is "1", in other words, the preceding rectangular pulse and the successive one which are both read with the grinding wheel 9 being at the same angular position are both "1", step 216 is executed to Judge whether (j) has reached a predetermined number (n=16 in this instance) of the grinding wheel rotations. When the answer at step 211 is NO, the address designated by the address pointer (k) is made to store "0" regardless of the status of the signal being stored at the same address. There comes to step 214 following to step 213 or 216. If (k) does not equal to (N), (k) is incremented at step 215, whereafter a sampled rectangular pulse S6 is read at step 210. When the grinding wheel 9 completes another full rotation, processing goes to step 216 to judge whether the grinding wheel rotations of n-times (i.e., 16 rotations) have been completed or not. If the answer is NO at step 216, processing moves to step 208 for storing the sampled rectangular pulses for 128 angular positions of the grinding wheel 9 during a still another or third rotation thereof. If "1" remains stored in any one of the 128-addresses of the memory area SRPM when the grinding wheel 9 completes the 16-rotations, processing is advanced from step 216 to step 218 wherein the grinding wheel 9 is judged to have contacted with the contact detection member 16. To the contrary, if "0" remains stored in all of the addresses of the memory area SRPM when the grinding wheel 9 completes the 16-full rotations, processing is advanced from step 217 to step 219, whereby the wheel head 7 is further advanced by predetermined feed amount, e.g., one micrometer from the contact detection start position.

In this manner, each time the grinding wheel 9 completes 16-full rotations, the contact between the grinding wheel 9 and the contact detection member 16 is ascertained by looking up the signal status of all the addresses of the memory area SRPM, and unless such contact is decided to have occurred, the wheel head 7 is advanced by another one micrometer. Finally, the occurrence of such contact is decided at step 218 in due course.

(Second Embodiment)

A second embodiment according to the present invention will be described with reference to FIGS. 7 to 11.

In the second embodiment, a setting circuit and second interface which respectively correspond to those in FIG. 1 are omitted as shown in FIG. 7 and the frequency of sampling pulses output from the sampling pulse generator 21b is determined in advance taking the rotational speed of the grinding wheel 9 into account. More specifically, the time period for which the grinding wheel 9 completes one full rotation is calculated from a rotational speed at which the grinding wheel 9 is set to rotate, and the frequency which is set to the sampling pulse generator 21b is determined so that the same outputs 256-sampling pulses within the calculated time period. The CPU 22b in this embodiment operates in accordance with the flow chart show in FIG. 8. In response to a detection cycle start command, the wheel head 7 is advanced at step 500 from a retracted position to a contact detection start position at which the grinding wheel 9 faces the contact detection member 16 with a small clearance (e.g., 5 to 10 micrometers). During the first rotation of the grinding wheel 9 subsequent thereto, 256 sampled pulses are read by the CPU 22b one after another and stored respectively at the first bits of address 1–256 of the memory area SRPM shown in FIG. 9. Successive 256 sampled pulses read during the second rotation of the grinding wheel 9 are stored respectively at the second bits of the addresses 1–256 of the memory area SRPM. Similar processing are repeated until all of the 16th bits of the addresses 1–256 complete storing the sampled rectangular pulses each "1" or "0".

Thereafter, a contact detection processing is executed at step 520 which is shown in detail in FIGS. 10(a) and 10(b). In this processing, the CPU 22b designates the first address of the memory area SRPM (step 521), ascertains whether "1" has been stored at all the bits of the designated address (step 522), stores "1" or "0" in an address of a summary memory area SMA (in FIG. 11) corresponding to the designated address, depending upon the judgement at step 522 (step 523 or 524), then increments the designated address (step 525) and repeats the step 522–526 if all the addresses of the memory area SRPM has not been designated (step 526). As a consequence, as shown FIG. 11, "1" is stored at each address of the summary memory area SMA only when "1" has been stored in all the bits of the address of the memory area SRPM which address corresponds to each such address of the summary memory area SMA. In the following steps 527 to 536, all the addresses of the summary memory area SMA is searched one after another for "1" signal. During this processing, when it is confirmed that "1" has been stored at each of successive addresses of a predetermined number (m=2, for example), the contact between the grinding wheel 9 and the contact detection member 16 is decided to have occurred (step 536). However, when it is not confirmed that the addresses each storing "1" of the summary memory area SMA are in succession in the predetermined number (m) even after all the addresses of the summary memory area SMA have been searched, such contact is decided not to have occurred (step 535), whereby the wheel head 7 is advanced by a unit distance (e.g., 1 micrometer) at step 540 of FIG. 8.

Therefore, steps 510, 520 and 540 are repetitively executed until it is decided at step 536 of FIG. 10(b) that the contact between the grinding wheel 9 and the contact detection member 16 has occurred. In short, in the second embodiment, the occurrence of such contact is decided when the grinding wheel 9 maintains its contact with the contact detection member 16 at the same two or more successive angular positions which are designated by the sampled rectangular pulses S6 from the pulse generator 21b throughout 16 rotations of the grinding wheel 9. Consequently, such contact can be reliably detected without suffering the influence by coolant, because it seldom occurs that all of the sampled rectangular pulses which are detected at the same successive angular positions of the grinding wheel 9 throughout the 16-rotations of the same are caused by coolant to indicate "1".

As a modification of the second embodiment, the predetermined number (m) may be set to 1, or steps 530–532 may be omitted. In this modification, such contact is decided to have occurred when it is confirmed that "1" has been stored at any one of the addresses of the summary memory area SMA.

(Third Embodiment)

A third embodiment of the present invention will be described with reference to FIGS. 1, 4, 12(a), 12(b) and 13.

The CPU 22b in this embodiment executes processings in accordance with the flow chart shown in FIG. 4, in the same manner as those described in connection with the first embodiment, except that at step 150, it executes the processing shown FIGS. 12(a) and 12(b) instead of that shown in FIGS. 5(a) and 5(b).

That is, when step 600 is reached, the wheel head 7 has been advanced to its contact detection start position and the setting circuit 21a has been set to make the sampling pulse generator 21b output 128-sampling pulses during one full rotation of the grinding wheel 9. At step 600, the wheel head 7 is advanced by a unit distance (e.g., 1 micrometer) from the contact detection start position, and the rotational number designation pointer (j) and an address pointer (k) are initialized to 1 (step 601 and 602). Each sampled rectangular pulse received from the interface 22a shown FIG. 1 is read at step 603, and if the read pulse indicates "0", step 608 follows wherein "0" is stored at one bit position which is of the address designated by the address pointer (k) and which is of those bits designated by the rotational number pointer (j). To the contrary, if the read pulse indicates "1", and if the rotational number pointer (j) indicates "1", step 607 is reached wherein "1" is stored at another bit position which is of the address designated by the pointer (k) and which is of those bits designated by the pointer (j). If the pointer (j) does not indicate "1", that is if the rotation of the grinding wheel 9 is not the first one, it is judged at step 606 whether "1" has been stored at any of those bit positions which are designated by the number (j–1) subtracted by one from that indicated by the pointer (j) and which are of those addresses designated by the pointer (k) or the number (k+1 or k–1) which results from adding 1 to, or subtracting 1 from, the number indicated by the pointer (k). Step 609 then follows from step 607 or 608 to ascertain whether processing for one rotation of the grinding wheel 9 has been completed or not. If the answer at step 609 is NO, the address pointer (k) is incremented at step 610 so as to then repeat the steps 603–609. As a result, during the first rotation of the grinding wheel 9, 128-sampled rectangular pulses each of which indicates the contact or non-contact of the grinding wheel 9 with the contact detection member 16 at 128 different angular positions of the grinding wheel 9 are stored respectively at the first bits of the 128-addresses of the memory area SRPM. During the second or subsequent rotation of the grinding wheel, each bit position designated by the pointers (k) and (j) comes to store "1" when a sampled rectangular pulse which is read at step 603 during the grinding wheel rotation of the j-th designated by the pointer (J) and at the rotational angular position designated by the pointer (k) indicates "1" and when any of the sampled rectangular pulses which are read during the preceding rotation of the grinding wheel 9 and at the same angular position of the same also indicates "1". Assuming now that the rectangular pulse which is detected with the grinding wheel 9 being at an angular position corresponding to the 3rd address of the memory area SRPM in FIG. 13 during the 2nd rotation of the grinding wheel 9 indicates "1", "1" is stored at the 2nd bit position of the 3rd address since "1" has been stored at the 1st bit position of the 2nd address of the memory area SRPM. As a result, "1" stored at the 16th bit position of any address of the memory area SRPM indicates that the contact between the grinding wheel 9 and the contact detection member 16 was made at the angular position of the grinding wheel 9 corresponding to any such address and at each of the 16-rotations of the grinding wheel 9.

Accordingly, when the grinding wheel 9 completes the 16-full rotations, processing is advanced from step 611 to step 613, wherein if it is ascertained by looking up all the 16th bit positions that "1" has been stored at least one of the 16th bit positions, the contact is decided to have occurred, and a contact detection signals made ON at step 614.

A modification of the third embodiment will be described with reference to FIGS. 14(a), 14(b) and 15. In this modification, the contact detection processing executed at step 150 in FIG. 4 is modified from the processing shown in FIGS. 12(a) and 12(b) to that shown in FIGS. 14(a) and 14(b), and a summary memory area SMA shown in FIG. 15 is used in place of the memory area SRPM shown in FIG. 13. Since the processing shown in FIGS. 14(a) and 14(b) is identical to that of the aforementioned first embodiment shown in FIGS. 5(a) and 5(b) except for steps 212a and 212b, description will be made hereafter as to the steps 212a and 212b.

That is, in this modification, when a sampled rectangular pulse read at step 210 during the second or subsequent rotation of the grinding wheel 9 is ascertained at step 211 to indicate "1", it is then ascertained at step 212a whether or not, either one address designated by the pointer (k) or one of two other addresses located at opposite sides of the designated one address has stored "1" therein, and if YES is answered at step 212a, step 212b is reached to store "1" at the address designated the pointer (k). As a result, upon completion of 16-full rotations of the grinding wheel 9, "1" may remain at least one addresses if a sampled rectangular pulse indicating "1" is successively detected during each of 16-rotations of the grinding wheel and at the same angular position as, or the next at either side to, the angular position at which the sampled rectangular pulse indicating "1" has been detected during the preceding rotation of the grinding wheel 9.

As described above, in the third embodiment and the modification thereof, the contact between the grinding wheel 9 and contact detection member 16 is decided to have occurred when the sampled signal "1" is detected at a certain angular position or the next thereto during each of the 16-full rotations of the grinding wheel 9.

(Fourth Embodiment)

A fourth embodiment of the present invention will be described with reference to FIGS. 16–18 and FIG. 3. In this embodiment, a comparator 20e outputs the rectangular pulse S4 shown in FIG. 3 to a first gate circuit 21e and also outputs a trigger pulse S7 whose width is considerably narrow compared with the rectangular pulse S4, to a second gate circuit 21c at the time when the pulse S4 trails. A rectangular width measuring circuit 121 is provided comprising a clock generator 21g, the first gate 21e, a counter 21f and the second gate circuit 21c. The first gate circuit 21e passes clock signal CK from the clock generator 21g to the counter 21f for the period of time corresponding to the duration of the rectangular pulse S4, whereby a count value which depends on the duration of the rectangular pulse S4 remains stored in the counter 21f until a next rectangular pulse S4 is issued from the comparator 20e. In response to the trigger pulse S7, the second gate circuit 21c passes the count value to the interface 22a. A signal processing circuit 122 includes a timing circuit 22e for generating timing pulses of a predetermined number at regular intervals while the grinding wheel 9 completes one-full rotation. The predetermined number coincides with the number of addresses of a pulse width memory area PWMA shown in FIG. 18.

Prior to the contact detection operation, the wheel head 7 is advanced from a retracted position to a contact detection start position, at which the grinding wheel 9 faces the contact detection member 16 with a small clearance such as several to ten micrometers therebetween. Then, the detection operation is initiated while the wheel head 7 is intermittently advanced by one micrometer at a time. During this detection operation, the CPU 22b successively reads the count values which are, in turn, applied from the counter 21f via the second gate circuit 21c to the interface 22a, in response to the timing pulses from the timing circuit 22e, whereby when the grinding wheel 9 completes one-full rotation, the count values each corresponding to the width of a rectangular pulse S4 associated therewith are stored at the memory addresses of the pulse width memory area PWMA, as shown in FIG. 18. Thereafter, the CPU 22b executes the processing shown in FIG. 17 for discriminating the actual contact of the grinding wheel 9 with the detection member 16 from disturbances primarily due to coolant.

That is, an address pointer (A), an effective count pointer (K) and a pulse width register (P) are initialized respectively at steps 450, 451 and 452. A count value (S) of an address designated by the address pointer (A) is read at step 453, and if the read value (S) is more than "0", the effective count pointer (K) is incremented at step 454. At the successive step 455, the count value (S) is added to the content of the pulse width register (P), which is thereby renewed. Step 456 follows either from step 453 or step 455 so as to increment the address pointer (A), and if the address designated by the pointer (A) does not indicate the final address, processing is returned from step 457 to step 453 to repeat those steps 453–457. Step 457 is followed by step 458, wherein a mean count value (R) is calculated by dividing the total count value (P) by the effective count number (K). The mean value (R) thus obtained represents a relatively large value when the contact between the grinding wheel 9 and the contact detection member 16 actually occurs, compared with that which is obtained when disturbance due to coolant is detected. Therefore, it is possible to discriminate such actual contact from the disturbance by comparing the mean value (R) with a reference value (M) at step 459, and if R>M, such contact is decided to have actually occurred at step 460.

If R>M does not hold, processing is returned to step 450, whereby step 450–459 are repetitively executed. Because the intermittent advancements of the wheel head 7 are carried out, the actual contact between the grinding wheel 9 and the contact detection member 16 occurs in due course and is decided to have occurred at step 460.

A modification of the aforementioned fourth embodiment will be described with reference to FIGS. 16 and 19. In this modification, the timing circuit 22e in FIG. 16 is arranged to operate as a timer for issuing a detection start pulse and a detection end pulse. The time interval between the two pulses is set longer than a time period for the grinding wheel 9 to complete at least one-full rotation. The CPU 22b in this modification executes the processing shown in FIG. 19 instead of that shown in FIG. 17, and the pulse width memory area PWMA shown in FIG. 18 is not used.

Likewise in the aforementioned fourth embodiment, the wheel head 7 is intermittently advanced by one micrometer at a time during the contact detection operation.

Upon starting of the detection operation, an effective count pointer (K) and a pulse width register (P) are initialized respectively at steps 570 and 571. The subsequent receipt of the detection start pulse from the timer 22e makes the processing move from step 572 to steps 573–576. Thus, a count value (S) from the counter 21f is read, the count pointer (K) is incremented and the content of the pulse width register (P) is renewed by the newly read count value (S) added thereto. Steps 573–576 are repeated until the CPU 22b receives the detection end pulse from the timer 22e, whereby the count value in the register (P) comes to represent a total contact time period within the duration taken for the grinding wheel 9 to complete one-full rotation. A mean contact time period (R) is then calculated at step 577 by dividing the total contact time period (P) by the effective count value of the pointer (K). The effective count value represents the number of times when a count value more than "0" is supplied from the counter 21f to the CPU 22b.

The actual contact between the grinding wheel 9 and the contact detection member 16 is decided at step 579 to have occurred as a result of comparing the mean contact time period (R) with a reference value (M), because the mean contact time period (R) obtained at the occurrence of an actual contact is relatively longer than that obtained at the occurrence of disturbance due to coolant.

(Fifth Embodiment)

Referring to FIGS. 20 and 21, there is shown a fifth embodiment of the present invention. A support member 17 is fixed to the head stock 5 by means of a bolt 44. A contact detection member 16' of this particular embodiment is held in an expansible hole of the support member 17 with a slot 43 and is secured by means of a bolt 42. The contact detection member 16' takes the form of a hollow pipe. Because of being a hollow pipe, the contact detection member 16' is reinforced against elastic deformation caused by the contact with the grinding wheel 9. Since cross-section area of the contact detection member 16' is minimized, the strength of the sound wave generated by the contact between the contact detection member 16' and the grinding wheel 9 is diminished. This makes the strength of the sound wave diminished also when coolant hits the contact detection member 16', so that precise contact detection can be realized. Further, a cylindrical dumping member 41 is arranged around the contact detection member 16' so as to absorb the vibration caused by coolant.

It is to be noted that the contact detection apparatus according to the present invention may be used also for any other rotating body than the grinding wheel 9. In other words, the application of the apparatus is not limited to grinding machines and rather, can be used for those machines of the type incorporating a rotating body.

It is also to be noted that during the contact detection operation, the wheel head 7 in any of the first to third embodiments may be arranged to be intermittently advanced by one micrometer at a time from a contact detection start position independently of the processings executed by the CPU 22b, in the same manner as described in connection with the fourth embodiment. In such modified cases, step 219 FIG. 5(a), step 540 in FIG. 8, step 600 in FIG. 12(a) and step 219 in FIG. 14(a) are omitted to advance the CPU's processing to the step successive thereto with doing nothing.

Obviously, numerous modifications and variations of the present invention are possible in light of the above teachings. It is therefore to be understood that within the scope of the appended claims, the present invention may be practiced otherwise than as specifically described herein.

What is claimed is:

1. An apparatus for detecting contact between a contact detection member and a rotating body, one of said contact detection member and said rotating body being moved toward an other of said contact detection member and said rotating body, comprising:

a sensor responsive to vibrations generated during a time period when said contact detection member is brought into contact with said rotating body for outputting an electric signal;

processing means responsive to said electric signal for processing said output to decide whether the detected contact has actually occurred or caused by disturbance, wherein said processing means comprises:

a) a memory having addresses dedicated to different angular positions of a sampling interval of said rotating body and storing at said addresses data based upon a value of said output, and b) decision means for deciding an occurrence of an actual contact between said rotating body and said contact detection member based on the values of data stored in said addresses of said memory.

2. An apparatus as set forth in claim 1, wherein said contact detection member comprises a hollow pipe which has said sensor secured to one end thereof and faces said rotating body at an other end thereof.

3. An apparatus as set forth in claim 2, further comprising:

a damping member provided around said hollow pipe for absorbing vibration generating on said hollow pipe.

4. The apparatus of claim 1 wherein said sampling interval comprises at least three rotations of said rotating body and said decision means for deciding the occurrence of an actual contact between said rotating body and said contact detection member comprises means for deciding the occurrence of contact when at least one of said addresses of said memory stores a value of said data indicative of a sensing of the vibrations by said sensor for at least the last two of at least three rotations of said sampling interval.

5. The apparatus of claim 4 wherein said at least the last two of said at least three rotations of said rotating body comprises all of said rotations of said sampling interval.

6. An apparatus for detecting contact between a contact detection member and a rotating body, one of said contact detection member and said rotating body being moved toward an other of said contact detection member and said rotating body, comprising:

a sensor responsive to vibrations generated during a time period when said contact detection member is brought into contact with said rotating body for outputting an electric signal;

processing means responsive to said electric signal for processing said output to decide whether the detected contact has actually occurred or caused by disturbance, wherein said processing means comprises:

a) a memory having addresses corresponding to different angular positions of a sampling interval of at least three rotations of said rotating body and storing at said addresses data based upon a value of said output, and b) decision means for deciding an occurrence of an actual contact between said rotating body and said contact detection member when, for all of said rotations of said sampling interval, one of said addresses, or addresses corresponding to angular positions adjacent the angular position to which said one address corresponds, stores data having a value indicative of a sensing of the vibrations by said sensor.

7. An apparatus for detecting contact between a contact detection member and a rotating body, one of said contact detection member and said rotating body being moved toward an other of said contact detection member and said rotating body, comprising:

- a sensor responsive to vibrations generated during a time period when said contact detection member is brought into contact with said rotating body for outputting an electric signal;
- rectangular pulse generating means responsive to said electric signal for generating a rectangular pulse having a duration corresponding to a time period of such contact;
- sampling means responsive to said rectangular pulse for delivering an output corresponding to said duration;
- processing means responsive to said output from said sampling means for processing said output to decide whether the detected contact has actually occurred or caused by disturbance, wherein said processing means comprises:

a) a memory having addresses corresponding to different angular positions of a sampling interval of said rotating body and storing at said addresses data based upon a value of said output, and b) decision means for deciding an occurrence of an actual contact between said rotating body and said contact detection member when the mean value of said data in all of said addresses exceeds a predetermined value.

* * * * *